United States Patent
Cesmeli

(12) 
(10) Patent No.: US 6,426,990 B1
(45) Date of Patent: Jul. 30, 2002

(54) METHODS AND APPARATUS FOR CORONARY-SPECIFIC IMAGING RECONSTRUCTION

(75) Inventor: Erdogan Cesmeli, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/681,944

(22) Filed: Jun. 28, 2001

(51) Int. Cl.$^7$ .................................. A61B 6/00
(52) U.S. Cl. .................................. 378/8; 378/4
(58) Field of Search .................. 378/8, 4, 19

(56) References Cited

U.S. PATENT DOCUMENTS

| | | | |
|---|---|---|---|
| 5,024,829 A | | 6/1991 | Berger et al. |
| 5,926,021 A | | 7/1999 | Hennig |
| 5,966,422 A | * | 10/1999 | Dafni et al. .................. 378/15 |
| 6,185,271 B1 | * | 2/2001 | Kinsinger .................. 378/19 |
| 6,198,959 B1 | | 3/2001 | Wang |
| 6,275,560 B1 | * | 8/2001 | Blake et al. .................. 378/8 |
| 6,275,720 B1 | | 8/2001 | Du et al. |
| 6,289,232 B1 | | 9/2001 | Jakob et al. |
| 6,292,684 B1 | | 9/2001 | Du et al. |
| 6,298,110 B1 | | 10/2001 | Ning |
| 6,298,259 B1 | | 10/2001 | Kucharczyk et al. |

\* cited by examiner

*Primary Examiner*—David P. Porta
*Assistant Examiner*—Pamela R. Hobden
(74) *Attorney, Agent, or Firm*—Armstrong Teasdale LLP

(57) ABSTRACT

One embodiment of the present invention provides a method for imaging a selected coronary artery utilizing a computed tomography (CT) imaging system. The method includes utilizing a data compilation of low motion cardiac phases and corresponding coronary artery branch segments to select a cardiac phase corresponding to the selected coronary artery branch segment. A volume of the patient's heart including the selected coronary artery branch segment is scanned to acquire projection data. The projection data includes data acquired during the selected cardiac phase of a plurality of cardiac cycles. Projection data acquired during the selected cardiac phase is selectively utilized to effectively reduce motion artifacts of the selected coronary artery branch segment on a reconstructed image.

26 Claims, 4 Drawing Sheets

METHODS AND APPARATUS FOR CORONARY-SPECIFIC IMAGING RECONSTRUCTION

BACKGROUND OF INVENTION

This invention relates generally to methods and apparatus for coronary imaging, and more particularly to methods and apparatus for computed tomographic (CT) imaging of specific artery branches with reduced motion artifacts.

Computed tomographic (CT) imaging and magnetic resonance imaging (MRI) can be utilized to visualize coronary arteries, which are very tiny structures. However, visualization of these structures is difficult, because different coronary arteries are subject to different motions throughout a cardiac cycle. For example, the right coronary artery (RCA) remains on a single plane and undergoes large displacements. The left anterior descending (LAD) vessel, on the other hand, lies on a curved surface and its branches follow different motion patterns. Known electrocardiograph (EKG) driven reconstruction methods and apparatus do not take these variations into account, so it has been difficult to achieve optimum visualization of at least some coronary arteries.

SUMMARY OF INVENTION

There is therefore provided, in one aspect, a method for imaging a selected coronary artery. The method utilizes a computed tomography (CT) imaging system having a rotating gantry, a detector array on the rotating gantry, and a radiation source on the rotating gantry configured to project a beam of radiation towards the detector array through a patient's heart. The method includes utilizing a data compilation of low motion cardiac phases and corresponding coronary artery branch segments to select a cardiac phase corresponding to the selected coronary artery branch segment. A volume of the patient's heart is scanned with the CT imaging system to acquire projection data. The volume includes at least the selected coronary artery branch segment, and the acquired projection data includes projection data acquired during the selected cardiac phase of a plurality of cardiac cycles of the patient. An image including at least the selected coronary artery branch segment is reconstructed, selectively utilizing the projection data acquired during the selected cardiac phase of the plurality of cardiac cycles to effectively reduce motion artifacts of the selected coronary artery branch segment on the reconstructed image.

In another aspect, a computed tomography (CT) imaging system is provided. The CT imaging system has a rotating gantry, a detector array on the rotating gantry, and a radiation source on the rotating gantry configured to project a beam of radiation towards the detector array through a patient's heart. The imaging system is configured to utilize a data compilation of low motion cardiac phases and corresponding coronary artery branch segments to select a cardiac phase corresponding to a selected coronary artery branch segment. The imaging system is also configured to scan a volume of the patient's heart to acquire projection data. The volume includes at least the selected coronary artery branch segment and the acquired projection data includes projection data acquired during the selected cardiac phase of a plurality of cardiac cycles of the patient. The imaging system is further configured to reconstruct an image including at least the selected coronary artery branch segment. For image reconstruction, the CT imaging system selectively utilizes the projection data acquired during the selected cardiac phase of the plurality of cardiac cycles to effectively reduce motion artifacts of the selected coronary artery branch segment on the reconstructed image.

In yet another aspect, a computer system is provided that is configured to utilize a data compilation of low motion cardiac phases and corresponding coronary artery branch segments to select a cardiac phase corresponding to a selected coronary artery branch segment. The computer system is further configured to read projection data acquired by a computed tomographic (CT) imaging system during a scan of a volume of a patient's heart. The volume represented by the projection data includes at least the selected coronary artery branch segment, and the acquired projection data includes projection data acquired during the selected cardiac phase of a plurality of cardiac cycles of the patient. The computer system is further configured to reconstruct an image including at least the selected coronary artery branch segment. To do so, the computer system is configured to selectively utilize the projection data acquired during the selected cardiac phase of the plurality of cardiac cycles to effectively reduce motion artifacts of the selected coronary artery branch segment on the reconstructed image.

In still another aspect, a machine readable medium having instructions recorded thereon is provided. The instructions are configured to instruct a computer to utilize a data compilation of low motion cardiac phases and corresponding coronary artery branch segments to select a cardiac phase corresponding to a selected coronary artery branch segment. In addition, the instructions are configured to instruct the computer to read projection data acquired by a computed tomographic (CT) imaging system during a scan of a volume of a patient's heart. This volume includes at least the selected coronary artery branch segment. The acquired projection data includes projection data acquired during the selected cardiac phase of a plurality of cardiac cycles of the patient. The instructions are additionally configured to instruct the computer to reconstruct an image including at least the selected coronary artery branch segment. To do so, the instructions are configured to instruct the computer to selectively utilize the projection data acquired during the selected cardiac phase of the plurality of cardiac cycles to effectively reduce motion artifacts of the selected coronary artery branch segment on the reconstructed image.

DETAILED DESCRIPTION

As used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) a viewable image. Included among the embodiments generating a viewable image are some that generate a plurality of images, each corresponding to a different z-axis location. Further as used herein, a "segment" of a coronary artery branch is considered as any portion of the branch that is adequately characterized, for image motion artifact reduction purposes, by a single low motion cardiac phase. Thus, it is not impossible that, in some cases, an entire branch may be considered as constituting a single segment.

In addition, as used herein, a "given" or "selected" cardiac phase refers to all or part of a contiguous range of phases around a targeted cardiac phase. The range is such that, were a sufficient number and angular range of views within the range available for a specified portion of the heart, that portion would appear sufficiently stationary such that a substantially artifact-free image could be reconstructed.

Figure 1:
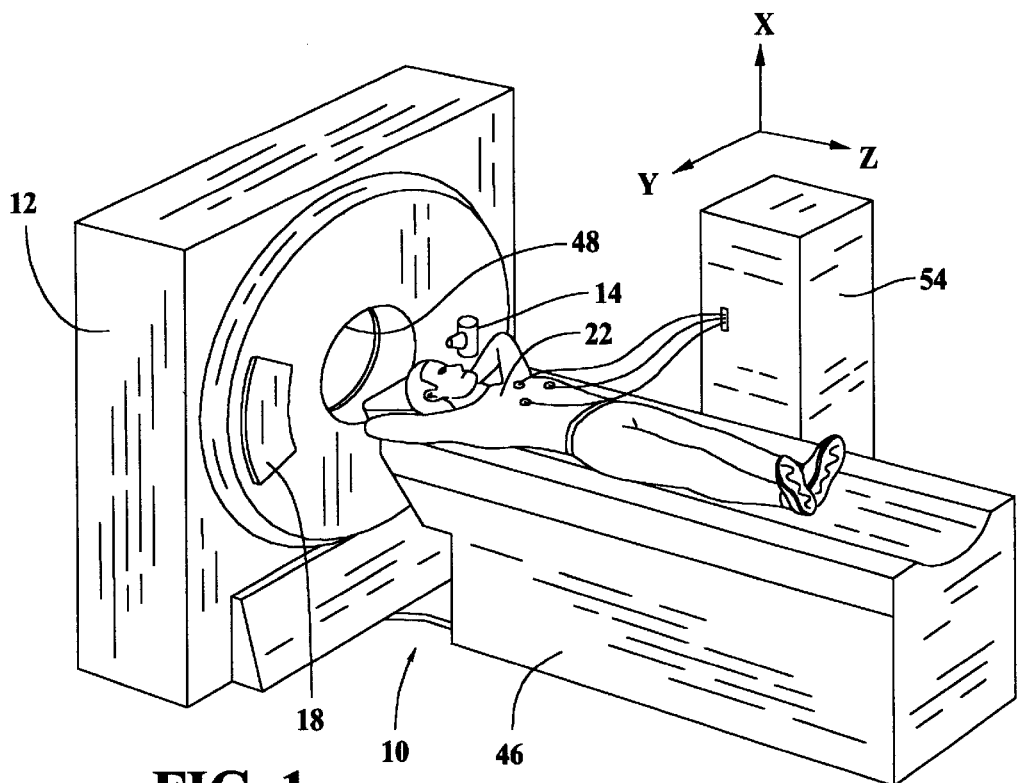
FIG. 1 is a pictorial view of a CT imaging system.
Figure 2:
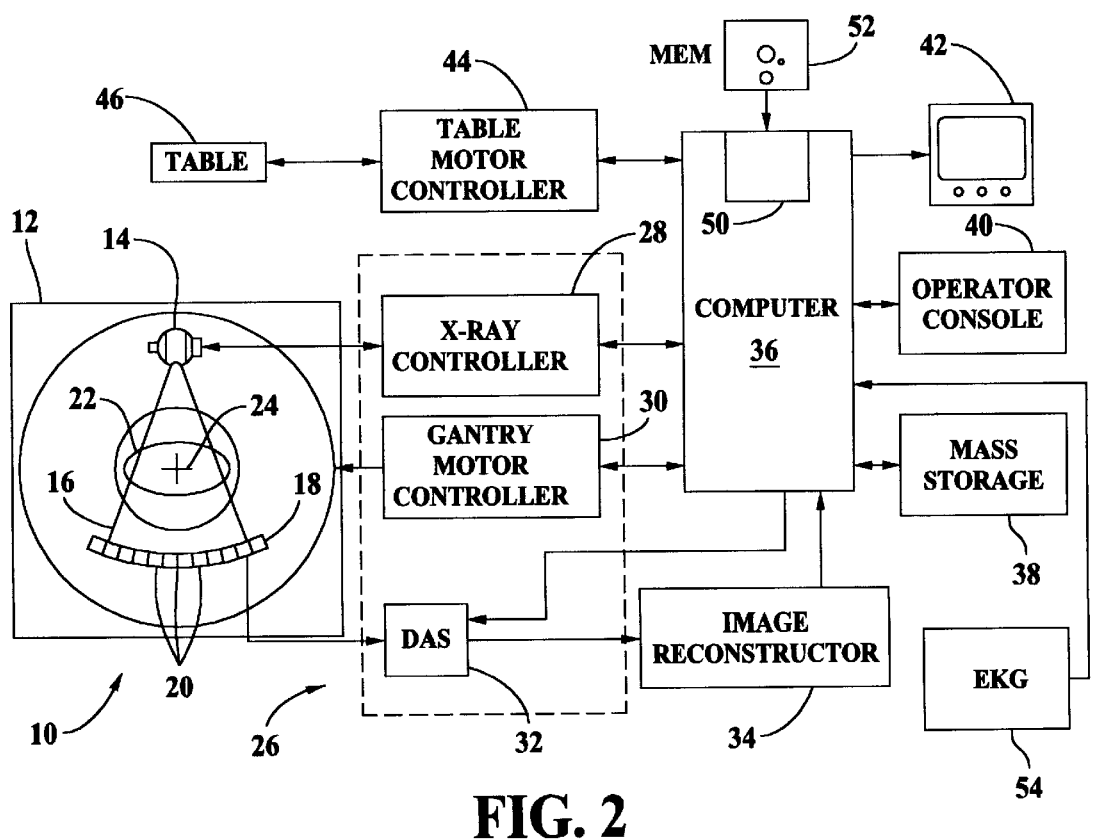
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has at least one x-ray radiation source 14 that projects a beam of x-ray radiation 16 toward a detector array 18 on the opposite side of gantry 12. Radiation beam 16 is, for example, a fan beam, a cone beam, or a parallel beam. Detector array 18 is formed by detector elements 20 that together sense the projected x-rays that pass through an object 22, for example a medical patient. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24. In one embodiment, detector array 18 is fabricated in a multi-slice configuration. In a multi-slice configuration, detector array 18 has a plurality of rows of detector elements or cells 20, only one of which is shown in FIG. 2. One or more additional rows of detector elements 20 in such configurations are arranged parallel to the illustrated row, and each row is transverse to the translation direction of patient 22 (i.e., the z-axis or patient axis).

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements or cells 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48. In a helical scan as performed in one embodiments of the present invention, table 46 moves while projection data is being collected and gantry 12 is rotating. The "helical pitch" is a measure of the amount of movement of table 46 per rotation of gantry 12.

In one embodiment, computer 36 includes a device 50 for reading and writing onto removable media 52. For example, device 50 is a floppy disk drive, a CD-R/W drive, or a DVD drive. Correspondingly, media 52 is either a floppy disk, a compact disk, or a DVD. Device 50 and media 52 are used in one embodiment to transfer acquired projection data from imaging system 10 to another computer for further processing, or in another embodiment to input machine readable instructions that are processed by computer 36.

Figure 3:
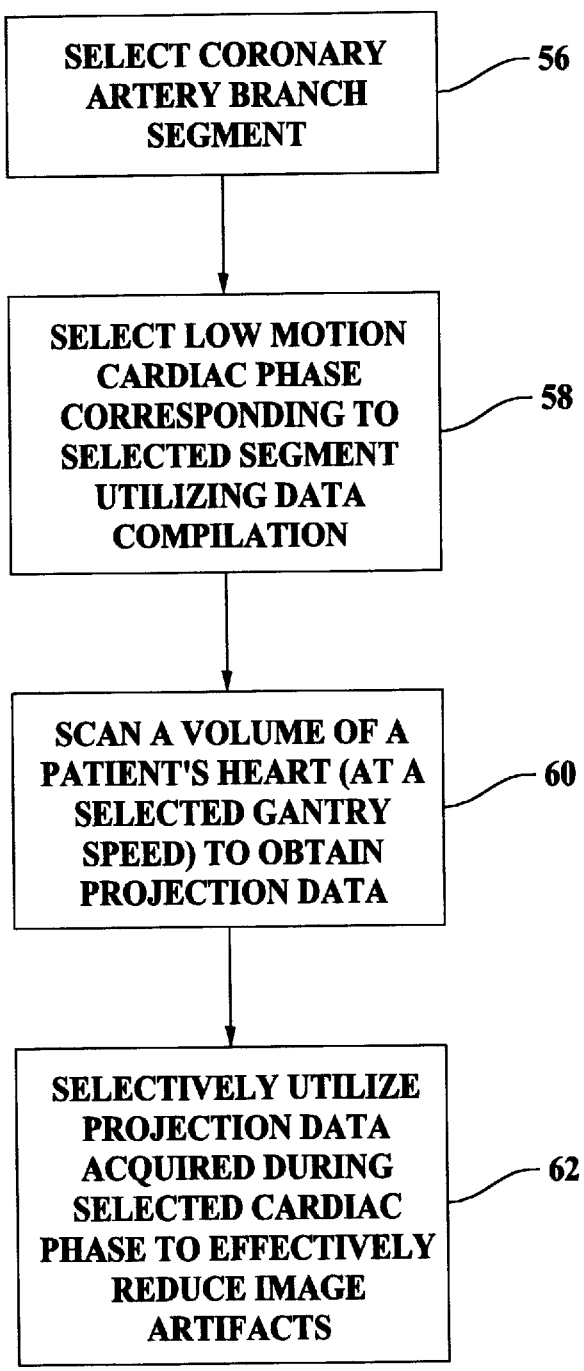
FIG. 3 is a flow chart representative of an embodiment of the present invention.

In one embodiment and referring to FIG. 3, a segment of a coronary artery branch of patient is selected 56 for imaging. A data compilation of coronary artery branch segments and their corresponding low motion cardiac phases is provided. Utilizing this data compilation, a low motion cardiac phase is selected 58 that corresponds to the selected coronary artery branch segment. A volume of the heart of patient 22 is then scanned 60 by imaging system 10 to acquire projection data. The volume scanned includes at least the selected coronary artery branch segment.

To facilitate image reconstruction, a rate of rotation of gantry 12 is set according to the cardiac cycle of the heart of patient 22, or to a measured average cardiac cycle rate. For example, computer 36 is used to detect occurrences of R peaks of an EKG measured by EKG machine 54, shown in FIG. 2. The rotation rate of gantry 12 is selected so that, at the same phase of different cardiac cycles, projection data is acquired from a variety of view angles. Projection data is collected from a sufficient range of view angles to reconstruct an image entirely from projection data acquired at the given cardiac phase. For a helical scan, a multislice detector array is used so that projection data at or near a plane of reconstruction (POR) is acquired by at least one detector row in different cardiac cycles as the scan proceeds.

In one embodiment, the projection data acquired during a scan includes projection data acquired during the selected cardiac phase of a plurality of different cardiac cycles of patient 22. This acquired projection data is used to reconstruct 62 an image of at least the selected coronary artery branch segment. In one embodiment, to effectively reduce motion artifacts of the selected coronary artery branch segment in the reconstructed image, only that projection data acquired during the selected cardiac phase (i.e., the small, contiguous range of phases referred to above) is utilized, to the exclusion of other projection data. Because different portions of the heart undergo minimum displacement velocities at different cardiac phases, the reconstructed image may not be optimized for all parts of the heart appearing in the image in all cases. However, a relatively artifact-free image is obtained of the selected coronary artery.

In another embodiment of the present invention, projection data acquired during the selected cardiac phase is used together with other projection data to reconstruct an image. However, to effectively reduce motion artifacts of the selected coronary artery branch segment in the reconstructed image, weights are applied to the projection data to more heavily weight the projection data acquired during the selected cardiac phase.

Identification and selection of projection data corresponding to a selected cardiac phase is facilitated by the simultaneous recording of an EKG signal from EKG machine 54 during acquisition of the projection data. For example, R peaks in a signal from EKG machine 54 are recorded and located by computer 36, and views of the projection data are tagged with numbers representing cardiac phases as a percentage of time between R peaks.

Although the cardiac periods of patients vary, a rest period of a particular segment of any given artery expressed as a percentage of a cycle type can be expected to be relatively constant. Thus, in one embodiment of the present invention, a data compilation of low motion cardiac phases corresponding to various coronary artery branch segments is derived from observations of a plurality of individuals. For example, low motion phases of a number of coronary arteries in different patients are observed from arteriograms collected from a plurality of individuals. The observed low motion phases (measured, for example, as a percent of a cardiac cycle from the most recent R peak of an EKG signal) are statistically combined, so that, for example, the data compilation contains low motion cardiac phases for each of the different observed cardiac artery branch segments, averaged over the plurality of patients observed. Methods such as those described by Wang et al. ("Cardiac Motion of Coronary Arteries: Variability in the Rest Period and Implications for Coronary MR Angiography," Radiology 1999, 213:751–758) are suitable for assembling a catalog of rest periods for segments of a collection of arteries as a percentage of the R-peak-to-R-peak time of an EKG. The data compilation can include, but does not have to be based upon observations of the patient being scanned. Thus, in one embodiment, the data compilation is based upon observations of a plurality of individuals that exclude observations of patient 22.

Figure 4:
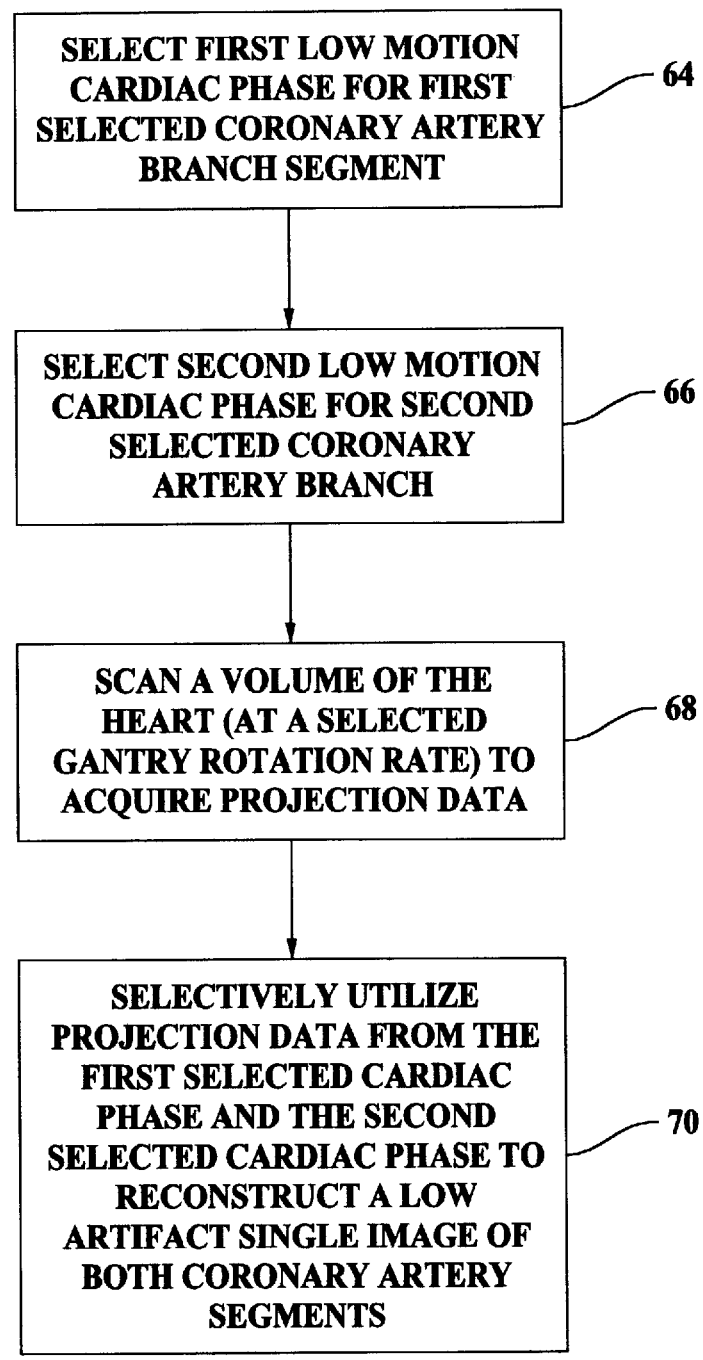
FIG. 4 is a flow chart representative of another embodiment of the present invention in which a composite image of an object is produced.

In some cases, low motion cardiac phases for different segments of the same coronary artery branch or of different coronary artery branches may be the same. In such cases, selection of a single low motion cardiac phase may suffice for artifact-free images of more than a single coronary artery branch segment. However, in some cases, it may be necessary or desirable to produce low artifact images of cardiac artery branch segments that have different low motion cardiac phases. Therefore, in one embodiment of the present invention and referring to FIG. 4, a first cardiac phase corresponding to a low motion period of a first selected coronary artery branch segment of the heart of patient 22 is selected 64. Also, a different, second cardiac phase corresponding to a second, different selected coronary artery branch segment is selected 66. A volume of the heart of patient 22 is scanned 68 using imaging system 10 to acquire projection data. The volume scanned includes at least the first selected coronary artery branch segment and the second selected coronary artery branch segment. Imaging system 10 thus acquires projection data that includes projection data representing the first selected coronary artery branch segment acquired during the first selected cardiac phase of a plurality of cardiac cycles of patient 22. The acquired projection data also includes projection data representing the second selected coronary artery branch segment acquired during the second selected cardiac phase of a plurality of cardiac cycles of patient 22. Using the acquired projection data, a single image including the first coronary artery branch segment and the second coronary artery branch segment of the heart of patient 22 is reconstructed 70.

Figure 5:
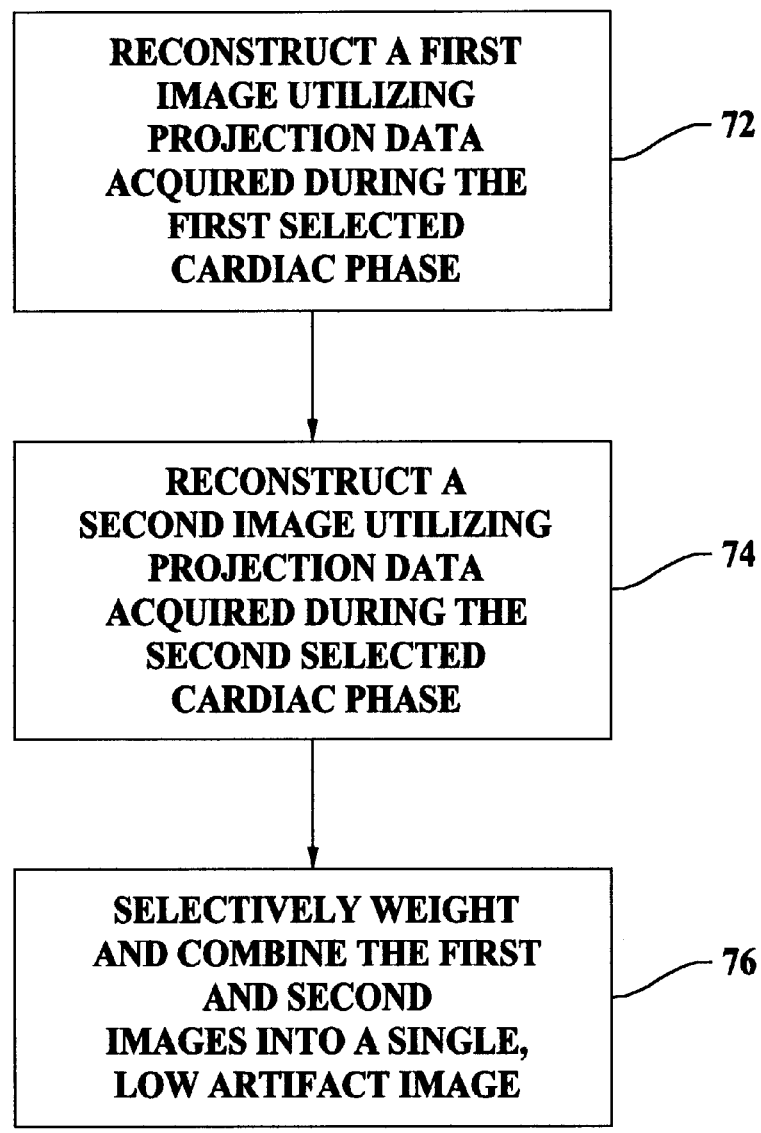
FIG. 5 is a flow chart representative of one technique for selectively utilizing projection data from a first cardiac phase and a second cardiac phase to produce a composite image.

The reconstruction selectively utilizes the projection data acquired during the first selected cardiac phase of a plurality of cardiac cycles to reduce motion artifacts of the first selected coronary artery branch segment on the single image. The reconstruction also selectively utilizes the projection data acquired during the second selected cardiac phase of a plurality of cardiac cycles to reduce motion artifacts of the second selected coronary artery branch segment on the single image. In one embodiment and referring to FIG. 5, the selective utilization of projection data comprises reconstructing 72 a first image including the first selected coronary artery branch segment utilizing projection data obtained only during the first selected cardiac phase of a plurality of cardiac cycles. In addition, a second image is reconstructed 74 including the second selected coronary artery branch segment utilizing projection data obtained only during the second selected cardiac phase of a plurality of cardiac cycles. The first image provides a low motion artifact portion that includes the first selected coronary artery branch segment, and the second image provides a low motion artifact portion that includes the second selected coronary artery branch segment. The two images are selectively weighted and combined 76 (e.g., "morphed") into the single image. The weighting and combining is such that, in a portion of the single image containing the first selected coronary artery branch segment, the contribution of the first image predominates. Similarly, in a portion of the second image containing the second selected coronary artery branch segment, the contribution of the second image predominates. In this manner, motion artifacts of both selected coronary artery branch segments are effectively reduced in the reconstructed single image.

In another embodiment, the projection data is selectively combined by differentially weighting the projection data acquired during the two different selected cardiac phases so that projection data acquired during the first cardiac phase in a plurality of cardiac cycles contributes more heavily in reconstruction to a portion of the image in which the first selected cardiac artery branch segment appears. Similarly, projection data acquired during the second cardiac phase in a plurality of cardiac cycles is weighted so that it contributes more heavily in reconstruction to a portion of the image in which the second selected cardiac artery branch segment appears.

The additional steps that are added to the above-described embodiments to extend their applicability to images having three or more selected coronary artery branch segments should, by now, be apparent to those skilled in the art. In general, an additional coronary artery phase is selected for each additional selected coronary artery branch segment.

Computer 36 and/or image reconstructor 34 of imaging system 10, either alone or in combination, provide the processing power necessary to perform the computational steps described above in at least one embodiment of the present invention. Instructions for performing the computational steps and the compilation of low motion cardiac phases corresponding to different coronary artery branch segments are stored in an associated memory, such as mass storage device 38, read only or read/write memory (not shown separately in FIG. 1), or media 52.

In at least one embodiment of the present invention, a computer system separate from imaging system 10 (for example, a workstation, not shown in the figures) is provided to reconstruct images using projection data acquired by imaging system 10. In these embodiments, acquired projection data and corresponding cardiac phase information is transferred from imaging system 10 to the separate computer system via a network (not shown) or suitable media 52. As a free-standing, separate computer system, these embodiments do not require a rotating gantry, a radiation source, or a detector array of their own. Also, these embodiments are configured to read or input projection data previously acquired by a CT imaging system. In other ways, they are configured in manners similar to the other apparatus embodiments discussed herein.

Other embodiments of the present invention include machine-readable media 52 having recorded thereon instructions configured to instruct a computer system to perform steps of one or more of the methods described herein.

The above-described embodiments will be recognized as achieving improved visualization of selected coronary artery branch segments as compared to known methods. Moreover, some of the above-described embodiments take into account variations in motion patterns between different coronary artery branch segments in a single image. These embodiments provide simultaneously improved visualization for both segments in a single image.

While the invention has been described in terms of various specific embodiments, those skilled in the art will recognize that the invention can be practiced with modification within the spirit and scope of the claims.

What is claimed is:

1. A method for imaging a selected coronary artery utilizing a computed tomography (CT) imaging system having a rotating gantry, a detector array on the rotating gantry, and a radiation source on the rotating gantry configured to project a beam of radiation towards the detector array through a patient's heart;

said method comprising:

utilizing a data compilation of low motion cardiac phases and corresponding coronary artery branch segments to select a cardiac phase corresponding to the selected coronary artery branch segment;

scanning a volume of the patient's heart with the CT imaging system to acquire projection data, the volume including at least the selected coronary artery branch segment and the acquired projection data including projection data acquired during the selected cardiac phase of a plurality of cardiac cycles of the patient; and reconstructing an image including at least the selected coronary artery branch segment, selectively utilizing the projection data acquired during the selected cardiac phase of the plurality of cardiac cycles to effectively reduce motion artifacts of the selected coronary artery branch segment on the reconstructed image.

2. A method in accordance with claim 1 wherein said reconstructing an image of the volume of the patient's heart comprises reconstructing the image without utilizing projection data other than the projection data acquired during the selected cardiac phase of the plurality of cardiac cycles.

3. A method in accordance with claim 1 wherein said data compilation of low motion cardiac phases and corresponding coronary artery branch segments is a data compilation derived from observations of a plurality of individuals.

4. A method in accordance with claim 3 wherein the observations of a plurality of individuals exclude observations of the patient.

5. A method for imaging a selected coronary artery or selected portion thereof utilizing a computed tomography (CT) imaging system having a rotating gantry, a detector array on the rotating gantry, and a radiation source on the rotating gantry configured to project a beam of radiation towards the detector array through a patient's heart;

said method comprising:

selecting a first cardiac phase corresponding to a low motion period of a first selected coronary artery branch segment of a patient's heart and a different, second cardiac phase corresponding to a second, different selected coronary artery branch segment of the patient's heart;

scanning a volume of the patient's heart with the CT imaging system to acquire projection data, the volume including at least the first selected coronary artery branch segment and the second selected coronary artery branch segment, and the acquired projection data including projection data representing the first selected coronary artery branch segment acquired during the first selected cardiac phase of a plurality of cardiac cycles of the patient and projection data representing the second selected coronary artery branch segment during the second selected cardiac phase of a plurality of cardiac cycles of the patient; and reconstructing a single image including the first selected coronary artery branch segment and the second selected coronary artery branch segment, selectively utilizing the projection data acquired during the first selected cardiac phase of a plurality of cardiac cycles to reduce motion artifacts of the first selected coronary artery branch segment and the projection data acquired during the second selected cardiac phase of a plurality of cardiac cycles to reduce motion artifacts of the second selected coronary artery branch segment on the blended image.

6. A method in accordance with claim 5 wherein said reconstructing a single image including the first selected coronary artery branch segment and the second coronary artery branch segment comprises reconstructing a first image excluding projection data other than the projection data acquired during the first selected cardiac phase of a plurality of cardiac cycles and a second image excluding projection data other than the projection data acquired during the second selected cardiac phase of a plurality of cardiac cycles, and selectively weighting and combining the first image and the second image to effectively reduce motion artifacts of both the first selected coronary artery and the second selected coronary artery in the single image.

7. A method in accordance with claim 5 wherein said reconstructing a single image including the first selected coronary artery branch segment and the second selected coronary artery branch segment comprises selectively utilizing the projection data acquired during the first selected cardiac phase of a plurality of cardiac cycles and the projection data acquired during the second selected cardiac phase of a plurality of cardiac cycles in reconstruction to effectively reduce motion artifacts of both the first selected coronary artery and the second selected coronary artery in the single image.

8. A computed tomography (CT) imaging system having a rotating gantry, a detector array on said rotating gantry, and a radiation source on said rotating gantry configured to project a beam of radiation towards said detector array through a patient's heart;

said system configured to:

utilize a data compilation of low motion cardiac phases and corresponding coronary artery branch segments to select a cardiac phase corresponding to a selected coronary artery branch segment;

scan a volume of the patient's heart to acquire projection data, the volume including at least the selected coronary artery branch segment and said acquired projection data including projection data acquired during said selected cardiac phase of a plurality of cardiac cycles of the patient; and reconstruct an image including at least the selected coronary artery branch segment, selectively utilizing said projection data acquired during said selected cardiac phase of the plurality of cardiac cycles to effectively reduce motion artifacts of the selected coronary artery branch segment on said reconstructed image.

9. A system in accordance with claim 8 wherein to reconstruct an image of the volume of the patient's heart, said system is configured to reconstruct said image without utilizing projection data other than said projection data acquired during said selected cardiac phase of the plurality of cardiac cycles.

10. A system in accordance with claim 8 wherein said data compilation of low motion cardiac phases and corresponding coronary artery branch segments is a data compilation derived from observations of a plurality of individuals.

11. A system in accordance with claim 10 wherein said data compilation is derived solely from individuals other than the patient.

12. A computed tomography (CT) imaging system having a rotating gantry, a detector array on the rotating gantry, and a radiation source on the rotating gantry configured to project a beam of radiation towards the detector array through a patient's heart;
said system configured to:
  select a first cardiac phase corresponding to a low motion period of a first selected coronary artery branch segment of the patient's heart and a different, second cardiac phase corresponding to a second, different selected coronary artery branch segment of the patient's heart;
  scan a volume of the patient's heart to acquire projection data, the volume including at least the first selected coronary artery branch segment and the second selected coronary artery branch segment, and said acquired projection data including projection data representing the first selected coronary artery branch segment acquired during said first selected cardiac phase of a plurality of cardiac cycles of the patient and projection data representing the second selected coronary artery branch segment during said second selected cardiac phase of a plurality of cardiac cycles of the patient; and
  reconstruct a single image including the first selected coronary artery branch segment and the second selected coronary artery branch segment, selectively utilizing said projection data acquired during said first selected cardiac phase of a plurality of cardiac cycles to reduce motion artifacts of the first selected coronary artery branch segment and said projection data acquired during said second selected cardiac phase of a plurality of cardiac cycles to reduce motion artifacts of the second selected coronary artery branch segment on said single image.

13. A system in accordance with claim 12 wherein to reconstruct said single image including the first selected coronary artery branch segment and the second coronary artery branch segment, said system is configured to reconstruct a first image excluding projection data other than said projection data acquired during the first selected cardiac phase of a plurality of cardiac cycles and a second image excluding projection data other than said projection data acquired during the second selected cardiac phase of a plurality of cardiac cycles, and selectively weight and combine said first image and said second image to effectively reduce motion artifacts of both the first selected coronary artery and the second selected coronary artery in said single image.

14. A system in accordance with claim 12 wherein to reconstruct said single image including the first selected coronary artery branch segment and the second selected coronary artery branch segment, said system is configured to selectively utilize said projection data acquired during the first selected cardiac phase of a plurality of cardiac cycles and said projection data acquired during the second selected cardiac phase of a plurality of cardiac cycles in reconstruction to effectively reduce motion artifacts of both the first selected coronary artery and the second selected coronary artery in said single image.

15. A computer system configured to:
  utilize a data compilation of low motion cardiac phases and corresponding coronary artery branch segments to select a cardiac phase corresponding to a selected coronary artery branch segment;
  read projection data acquired by a computed tomographic (CT) imaging system during a scan of a volume of a patient's heart, the volume including at least the selected coronary artery branch segment and the acquired projection data including projection data acquired during said selected cardiac phase of a plurality of cardiac cycles of the patient; and
  reconstruct an image including at least the selected coronary artery branch segment, selectively utilizing the projection data acquired during said selected cardiac phase of the plurality of cardiac cycles to effectively reduce motion artifacts of the selected coronary artery branch segment on said reconstructed image.

16. A computer system in accordance with claim 15 wherein to reconstruct an image of the volume of the patient's heart, said computer system is configured to reconstruct said image without utilizing projection data other than the projection data acquired during said selected cardiac phase of the plurality of cardiac cycles.

17. A computer system in accordance with claim 15 wherein said data compilation of low motion cardiac phases and corresponding coronary artery branch segments is a data compilation derived from observations of a plurality of individuals.

18. A computer system in accordance with claim 17 wherein said data compilation is derived solely from individuals other than the patient.

19. A computer system configured to:
  select a first cardiac phase corresponding to a low motion period of a first selected coronary artery branch segment of the patient's heart and a different, second cardiac phase corresponding to a second, different selected coronary artery branch segment of the patient's heart;
  read projection data acquired by a computed tomographic (CT) imaging system during a scan of a volume of a patient's heart, the volume including at least the first selected coronary artery branch segment and the second selected coronary artery branch segment, and the acquired projection data including projection data representing the first selected coronary artery branch segment acquired during said first selected cardiac phase of a plurality of cardiac cycles of the patient and projection data representing the second selected coronary artery branch segment during said second selected cardiac phase of a plurality of cardiac cycles of the patient; and
  reconstruct a single image including the first selected coronary artery branch segment and the second selected coronary artery branch segment, selectively utilizing the projection data acquired during said first selected cardiac phase of a plurality of cardiac cycles to reduce motion artifacts of the first selected coronary artery branch segment and the projection data acquired during said second selected cardiac phase of a plurality of cardiac cycles to reduce motion artifacts of the second selected coronary artery branch segment on said single image.

20. A computer system in accordance with claim 19 wherein to reconstruct said single image including the first selected coronary artery branch segment and the second coronary artery branch segment, said computer system is configured to reconstruct a first image excluding projection data other than the projection data acquired during the first selected cardiac phase of a plurality of cardiac cycles and a second image excluding projection data other than the projection data acquired during the second selected cardiac phase of a plurality of cardiac cycles, and selectively weight and combine said first image and said second image to effectively reduce motion artifacts of both the first selected coronary artery and the second selected coronary artery in said single image.

21. A computer system in accordance with claim 19 wherein to reconstruct said single image including the first selected coronary artery branch segment and the second selected coronary artery branch segment, said computer system is configured to selectively utilize the projection data acquired during the first selected cardiac phase of a plurality of cardiac cycles and the projection data acquired during the second selected cardiac phase of a plurality of cardiac cycles in reconstruction to effectively reduce motion artifacts of both the first selected coronary artery and the second selected coronary artery in said single image.

22. A machine readable medium having instructions recorded thereon configured to instruct a computer to:
  utilize a data compilation of low motion cardiac phases and corresponding coronary artery branch segments to select a cardiac phase corresponding to a selected coronary artery branch segment;
  read projection data acquired by a computed tomographic (CT) imaging system during a scan of a volume of a patient's heart, the volume including at least the selected coronary artery branch segment and the acquired projection data including projection data acquired during said selected cardiac phase of a plurality of cardiac cycles of the patient; and
  reconstruct an image including at least the selected coronary artery branch segment, selectively utilizing the projection data acquired during said selected cardiac phase of the plurality of cardiac cycles to effectively reduce motion artifacts of the selected coronary artery branch segment on said reconstructed image.

23. A machine readable medium in accordance with claim 22 wherein to reconstruct an image of the volume of the patient's heart, said machine readable medium has recorded thereon instructions configured to instruct the computer to reconstruct said image without utilizing projection data other than the projection data acquired during said selected cardiac phase of the plurality of cardiac cycles.

24. A machine readable medium having instructions recorded thereon configured to instruct a computer to:
  select a first cardiac phase corresponding to a low motion period of a first selected coronary artery branch segment of the patient's heart and a different, second cardiac phase corresponding to a second, different selected coronary artery branch segment of the patient's heart;
  read projection data acquired by a computed tomographic (CT) imaging system during a scan of a volume of a patient's heart, the volume including at least the first selected coronary artery branch segment and the second selected coronary artery branch segment, and the acquired projection data including projection data representing the first selected coronary artery branch segment acquired during said first selected cardiac phase of a plurality of cardiac cycles of the patient and projection data representing the second selected coronary artery branch segment during said second selected cardiac phase of a plurality of cardiac cycles of the patient; and
  reconstruct a single image including the first selected coronary artery branch segment and the second selected coronary artery branch segment, selectively utilizing the projection data acquired during said first selected cardiac phase of a plurality of cardiac cycles to reduce motion artifacts of the first selected coronary artery branch segment and the projection data acquired during said second selected cardiac phase of a plurality of cardiac cycles to reduce motion artifacts of the second selected coronary artery branch segment on said single image.

25. A machine readable medium in accordance with claim 24 wherein to reconstruct said single image including the first selected coronary artery branch segment and the second coronary artery branch segment, said machine readable medium has recorded thereon instructions configured to instruct the computer to reconstruct a first image excluding projection data other than the projection data acquired during the first selected cardiac phase of a plurality of cardiac cycles and a second image excluding projection data other than the projection data acquired during the second selected cardiac phase of a plurality of cardiac cycles, and selectively weight and combine said first image and said second image to effectively reduce motion artifacts of both the first selected coronary artery and the second selected coronary artery in said single image.

26. A machine readable medium in accordance with claim 24 wherein to reconstruct said single image including the first selected coronary artery branch segment and the second selected coronary artery branch segment, said machine readable medium has recorded thereon instructions configured to instruct the computer to selectively utilize the projection data acquired during the first selected cardiac phase of a plurality of cardiac cycles and the projection data acquired during the second selected cardiac phase of a plurality of cardiac cycles in reconstruction to effectively reduce motion artifacts of both the first selected coronary artery and the second selected coronary artery in said single image.

* * * * *